United States Patent
Lennox et al.

(10) Patent No.: US 6,478,939 B1
(45) Date of Patent: *Nov. 12, 2002

(54) BIOSENSOR DEVICE AND METHOD

(75) Inventors: R. Bruce Lennox, Montreal (CA);
Robert S. Hodges, Edmonton (CA);
Randall T. Irvin, Sherwood Park (CA)

(73) Assignees: Pence, Inc., Edmonton (CA); McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/578,353

(22) Filed: May 24, 2000

Related U.S. Application Data

(62) Division of application No. 08/845,660, filed on Apr. 24, 1997, now Pat. No. 6,165,335.
(60) Provisional application No. 60/016,196, filed on Apr. 25, 1996, and provisional application No. 60/016,385, filed on Apr. 25, 1996.

(51) Int. Cl.[7] .......................... G01N 27/26; G01N 21/00
(52) U.S. Cl. ........................ 204/403.08; 204/403.01; 204/418; 436/164
(58) Field of Search .................. 204/403, 416, 204/418, 403.01, 403.08; 435/817; 436/164, 172, 908

(56) References Cited

U.S. PATENT DOCUMENTS 3,891,507 A    6/1975  Breuer (List continued on next page.)

FOREIGN PATENT DOCUMENTS

| EP | 505 494 B1 | 7/1995 |
|---|---|---|
| WO | WO 89/01159 | 2/1989 |
| WO | WO 90/05303 | 5/1990 |
| WO | WO 93/15110 | 8/1993 |
| WO | WO 95/31480 | 11/1995 |
| WO | WO 96/02830 | 2/1996 |
| WO | WO 96/09547 | 3/1996 |
| WO | WO 96/10178 | 4/1996 |
| WO | WO 97/01092 | 1/1997 |
| WO | WO 97/02359 | 1/1997 |
| WO | WO 97/07593 | 2/1997 |
| WO | WO 97/41424 | 11/1997 |
| WO | WO 97/41425 | 11/1997 |

OTHER PUBLICATIONS

Chao et al. "Kinetic Study on the Formation of a de Novo Designed Heterodimeric Coiled–Coil Use of Surface Plasmon Resonance To Monitor the association and Dissociation of POlypeptide Chains", Biochemistry 1996, 35, 12175–12185.*

Chao et al. "Use of a heterodimeric coiled–coil system for biosensor application and affinity purification", Journal of Chromatography B, 715 (1998) 307–329.*

(List continued on next page.)

*Primary Examiner*—Jill Warden
*Assistant Examiner*—Alex Noguerola
(74) *Attorney, Agent, or Firm*—Perkins Coie LLP; Peter J. Dehlinger; Larry W. Thrower

(57) ABSTRACT

A biosensor apparatus for detecting a binding event between a ligand and receptor. The apparatus includes a biosensor surface and surface-bound two-subunit heterodimer complexes composed of first and second, preferably oppositely charged peptides that together form an α-helical coiled-coil heterodimer. The first peptide is attached to the biosensor surface, and the second peptide carries the ligand, accessible for binding by a ligand-binding agent. Binding of anti-ligand binding agent to the surface-bound ligand is detected by a suitable detector. A ligand-specific biosensor surface can be readily prepared from a universal template containing the first charged peptide, by addition of a selected ligand attached to the second peptide.

8 Claims, 10 Drawing Sheets

U.S. PATENT DOCUMENTS

| | | |
|---|---|---|
| 3,990,850 A | 11/1976 | Friedman et al. |
| 4,038,030 A | 7/1977 | Albright et al. |
| 4,789,804 A | 12/1988 | Karube et al. |
| 4,945,045 A | 7/1990 | Forrest et al. |
| 5,078,855 A | 1/1992 | Mochizuki et al. |
| 5,089,112 A | 2/1992 | Skotheim et al. |
| 5,104,619 A | 4/1992 | de Castro et al. |
| 5,116,481 A | 5/1992 | Ozawa et al. |
| 5,192,507 A | 3/1993 | Taylor et al. |
| 5,200,051 A | 4/1993 | Cozzette et al. |
| 5,242,828 A | 9/1993 | Bergström et al. |
| 5,246,846 A | 9/1993 | Pittner et al. |
| 5,268,305 A | 12/1993 | Ribi et al. |
| 5,313,264 A | 5/1994 | Ivarsson et al. |
| 5,368,712 A | 11/1994 | Tomich et al. |
| 5,401,378 A | 3/1995 | King et al. |
| 5,405,783 A | 4/1995 | Pirrung et al. |
| 5,436,161 A | 7/1995 | Bergström et al. |
| 5,436,170 A | 7/1995 | Cornell et al. |
| 5,478,756 A | 12/1995 | Gizeli et al. |
| 5,485,277 A | 1/1996 | Foster |
| 5,491,097 A | 2/1996 | Ribi et al. |
| 5,492,840 A | 2/1996 | Malmqvist et al. |
| 5,514,501 A | 5/1996 | Tarlov |
| 5,527,711 A | 6/1996 | Tom-Moy et al. |
| 5,567,301 A | 10/1996 | Stetter et al. |
| 5,571,568 A | 11/1996 | Ribi et al. |
| 5,580,794 A | 12/1996 | Allen |
| 5,622,872 A | 4/1997 | Ribi |
| 5,624,537 A | 4/1997 | Turner et al. |
| 5,637,201 A | 6/1997 | Raguse et al. |
| 5,693,477 A | 12/1997 | Cornell et al. |
| 5,707,502 A | 1/1998 | McCaffrey et al. |
| 5,723,345 A | 3/1998 | Yamauchi et al. |
| 5,736,410 A | 4/1998 | Zarling et al. |
| 5,741,409 A | 4/1998 | Raguse et al. |
| 5,753,093 A | 5/1998 | Raguse et al. |
| 5,756,355 A | 5/1998 | Lang et al. |
| 5,783,054 A | 7/1998 | Raguse et al. |
| 5,798,030 A | 8/1998 | Raguse et al. |
| 5,824,483 A | 10/1998 | Houston, Jr. et al. |
| 5,834,224 A | 11/1998 | Ruger et al. |
| 5,942,388 A | 8/1999 | Willner et al. |
| 5,955,379 A | 9/1999 | Lennox et al. |
| 6,074,616 A | 6/2000 | Beuchler et al. |
| 6,096,825 A | 8/2000 | Garnier |
| 6,165,335 A * | 12/2000 | Lennox et al. .............. 204/403 |

OTHER PUBLICATIONS

Adamson, J.G., et al., "Structure, function and application of the coiled–coil protein folding motif" *Current Opinion in Biotechnology* 4:428–437 (1993), month unknown.

Blondel, A. and Bedouelle, H., "Engineering the quaternary structure of an exported protein with a leucine zipper" *Protein Engineering* 4(4): 457–461 (1991), month unknown.

Hu, J.C., et al., "Sequence Requirements for Coiled–Coils: Analysis with λ Repressor–GCN4 Leucine Zipper Fusions" *Science* 250:1400–1403 Dec. (1990).

Khilko, S.N., et al., "Measuring interactions of MHC class I molecules using surface plasmon resonance" *J. Immunological Methods* 183:77–94 (1995).

Monera, O.D., et al., "Electrostatic Interactions Control the Parallel and Antiparallel Orientation of α–Helical Chains in Two–Stranded α–Helical Coiled–Coils" *Biochemistry* 33:3862–3871 ( (1994), month unknown.

O'Shea, E.K., et al., "Peptide 'Velcro*': design of a heterodimeric coiled coil" *Current Biology* 3:658–667 (1993), month unknown.

Zhou, N.E., et al., "The Two–Stranded α–Helical Coiled–Coil Is an Ideal Model for Studying Protein Stability and Subunit Interactions" *Biopolymers* 32:419–426 (1992).

* cited by examiner

Homodimers | Heterodimers

Stabilized

Destabilized

Destabilized

Stabilized

Destabilized

BIOSENSOR DEVICE AND METHOD

This application is a division of U.S. application Ser. No. 08/845,660 filed Apr. 24, 1997, which is now U.S. Pat. No. 6,165,335 which claims the priority of U.S. Provisional Application No. 60/016,196, filed Apr. 25, 1996, and U.S. Provisional Application No. 60/016,385, filed Apr. 25, 1996, which are incorporated herein by reference.

FIELD OF THE INVENTION

The present invention relates to biosensors, and in particular, to a biosensor for measuring a binding event between a ligand and a ligand-binding receptor, and to methods for producing such biosensors.

BACKGROUND OF THE INVENTION

Diagnostic tools used for detecting or quantitating biological analytes typically rely on ligand-specific binding between a ligand and a receptor. Ligand/receptor binding pairs used commonly in diagnostics include antigen-antibody, hormone-receptor, drug-receptor, cell surface antigen-lectin, biotin-avidin, substrate/enzyme, and complementary nucleic acid strands. The analyte to be detected may be either member of the binding pair; alternatively, the analyte may be a ligand analog that competes with the ligand for binding to the complement receptor.

A variety of devices for detecting ligand/receptor interactions are known. The most basic of these are purely chemical/enzymatic assays in which the presence or amount of analyte is detected by measuring or quantitating a detectable reaction product, such as gold immunoparticles. Ligand/receptor interactions can also be detected and quantitated by radiolabel assays.

Quantitative binding assays of this type involve two separate components: a reaction substrate, e.g., a solid-phase test strip and a separate reader or detector device, such as a scintillation counter or spectrophotometer. The substrate is generally unsuited to multiple assays, or to miniaturization, for handling multiple analyte assays from a small amount of body-fluid sample.

In biosensor diagnostic devices, by contrast, the assay substrate and detector surface are integrated into a single device. One general type of biosensor employs an electrode surface in combination with current or impedance measuring elements for detecting a change in current or impedance in response to the presence of a ligand-receptor binding event. This type of biosensor is disclosed, for example, in U.S. Pat. No. 5,567,301.

Gravimetric biosensors employ a piezoelectric crystal to generate a surface acoustic wave whose frequency, wavelength and/or resonance state are sensitive to surface mass on the crystal surface. The shift in acoustic wave properties is therefore indicative of a change in surface mass, e.g., due to a ligand-receptor binding event. U.S. Pat. Nos. 5,478,756 and 4,789,804 describe gravimetric biosensors of this type.

Biosensors based on surface plasmon resonance (SPR) effects have also been proposed, for example, in U.S. Pat. Nos. 5,485,277 and 5,492,840. These devices exploit the shift in SPR surface reflection angle that occurs with perturbations, e.g., binding events, at the SPR interface. Finally, a variety of biosensors that utilize changes in optical properties at a biosensor surface are known, e.g., U.S. Pat. No. 5,268,305.

Biosensors have a number of potential advantages over binding assay systems having separate reaction substrates and reader devices. One important advantage is the ability to manufacture small-scale, but highly reproducible, biosensor units using microchip manufacturing methods, as described, for example, in U.S. Pat. Nos. 5,200,051 and 5,212,050.

Another advantage is the potentially large number of different analyte detection regions that can be integrated into a single biosensor unit, allowing sensitive detection of several analytes with a very small amount of body-fluid sample. Both of these advantages can lead to substantial cost-per-test savings.

A key element in the manufacture of biosensors, particularly multi-assay biosensors, is the placement of analyte-specific binding molecules or enzymes at desired locations on a biosensor surface. Ideally, it would be desirable to construct a universal biosensor surface under rigorous microchip manufacturing conditions, but allow a variety of different surface-region formats to be achieved under less restrictive manufacturing conditions, which at one extreme would allow an end user to tailor the universal chip to a unique multi-analyte format.

SUMMARY OF THE INVENTION

In one aspect, the invention includes a biosensor apparatus for detecting a binding event between a ligand and ligand-binding agent. The apparatus has a biosensor surface, and two-subunit heterodimer complexes carried on the surface. The complexes are composed of first and second, preferably oppositely charged peptides that together form an α-helical coiled-coil heterodimer. The first peptide is attached to the biosensor surface, and a ligand is covalently attached to the second peptide, accessible for binding by a ligand-binding agent. Binding of an anti-ligand agent to the ligand is detected by a suitable detector in the apparatus.

The first peptide subunit may be attached to the biosensor surface covalently, e.g., through an oligopeptide spacer or a hydrocarbon-chain spacer, or may be bound to the biosensor surface through a stable non-covalent linkage, e.g., a biotin/avidin binding pair. The biosensor surface may include multiple regions, each having a different selected ligand attached to the second-subunit peptide.

In one general embodiment, the biosensor surface includes a monolayer composed of hydrocarbon chains anchored at their proximal ends to the biosensor surface, and having free distal ends defining an exposed monolayer surface. The heterodimer complexes in this embodiment are preferably embedded in the monolayer, and the ligands are disposed on or near the monolayer surface. The monolayer may be formed on a metal, e.g., gold film, and may be composed of 8–22 carbon atom chains attached at their proximal ends to the biosensor surface by a thiol linkage. The chains have a preferred molecular density of about 3 to 5 chains/nm$^2$, and the dielectric constant of the monolayer, in the presence of such solution but in the absence of such binding receptor, is preferably less than about 2.

In a biosensor apparatus designed for amperometric detection of binding of a ligand-binding agent to the monolayer ligand, the biosensor surface is an electrode, and the monolayer, including the heterodimer complexes embedded in the monolayer, is sufficiently close-packed and ordered to form an effective barrier to current across the monolayer mediated by a redox ion species in an aqueous solution in contact with the monolayer. Binding of a ligand-binding agent to the ligand on the monolayer surface is effective to increase current across the monolayer, mediated by such redox species. A chamber in the apparatus is adapted to contain an aqueous solution of redox species in contact with the monolayer, and the detector includes a circuit for measuring ion-mediated current across the monolayer, in response to binding events occurring between the receptor and ligand.

In a biosensor apparatus designed for gravimetric detection of binding of a ligand-binding agent to the surface-bound ligand, the biosensor surface is a piezoelectric crystal. The detector functions to (i) generate a surface acoustic wave in the crystal and (ii) detect the shift in wave frequency, velocity, or resonance frequency of the surface acoustic wave produced by binding of ligand-binding agent to the ligand.

In a biosensor designed for optical surface plasmon resonance (SPR) detection of binding of a ligand-binding agent to the surface-bound ligand, the biosensor surface is a transparent dielectric substrate coated with a thin metal layer on which the monolayer is formed, where the substrate and metal layer form a plasmon resonance interface. The detector functions to excite surface plasmons at a plasmon resonance angle that is dependent on the optical properties of the metal film and attached monolayer, and to detect the shift in plasmon resonance angle produced by binding of ligand-binding agent to the ligand.

In a biosensor designed for optical detection of binding of a ligand-binding agent to the surface bound ligand, the detector functions to irradiate the biosensor surface with a light beam, and detect a change in the optical properties of the surface layer, e.g., monolayer with embedded heterodimer, produced by binding of ligand-binding agent to the ligand.

In another aspect, the invention includes a method for producing a ligand-specific biosensor for use in a biosensor apparatus capable of detecting a binding event between a ligand and ligand-binding receptor. The method involves contacting together: (a) a biosensor electrode having a biosensor surface and a first heterodimer-subunit peptide attached to the biosensor surface, and (b) a second, preferably oppositely charged peptide capable of binding to the first peptide to form a two-subunit α-helical coiled-coil heterodimer. The second peptide has an attached ligand capable of binding specifically to a ligand-specific agent. The contacting is effective attach ligands to the biosensor surface. The biosensor surface may include first and second discrete regions, where the second heterodimer subunit peptide in each region has a different attached ligand.

In one general embodiment of the method, the biosensor surface has a monolayer composed of hydrocarbon chains (i) anchored at their proximal ends to the biosensor surface, and (ii) having free distal ends defining an exposed monolayer surface. The first peptide is embedded in the monolayer, and binding of the second peptide to surface-bound first peptide is effective to dispose the ligand preferably on or near the monolayer surface.

More generally, the invention provides a method of constructing an array of different, selected biological reagents attached to different, selected regions on an assay support surface. The method includes attaching molecules of a first heterodimer-subunit peptide to the support surface, effective to cover the different regions on the surface with the first peptide molecules. The subunit peptide has protecting groups which when photo-released, allow the peptide to interact with a second, preferably oppositely charged heterodimer-subunit peptide, to form a two-subunit α-helical coiled-coil heterodimer.

The surface is irradiated in a selected region of the surface under conditions effective to deprotect the first peptide in the irradiated region only, then contacted with a second subunit peptide carrying the assay reagent. This contacting is effective to attach the selected reagent to the exposed region of the surface only. The above steps are repeated for different selected regions and assay reagents, until the desired array of different, selected biological reagents disposed at different selected regions on an assay support surface is produced.

In one embodiment, the first subunit peptide contains amino acid residues with one or more protected carboxyl groups, e.g., glutamate groups with nitrophenolate protecting groups.

These and other objects and features of the invention will become more fully apparent when the following detailed description of the invention is read in conjunction with the accompanying drawings.

DETAILED DESCRIPTION OF THE INVENTION

I. Biosensor Apparatus

Figure 1A:
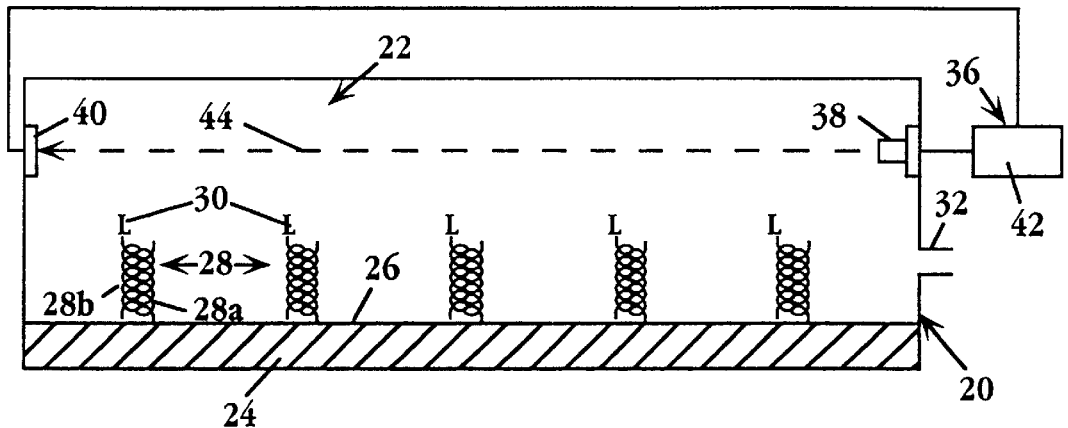
FIGS. 1A and 1B show elements of a biosensor apparatus in accordance with of the invention, illustrating the apparatus before (1A) and after (1B) binding of a ligand-binding agent to the biosensor surface in the apparatus.
Figure 1B:
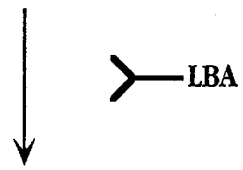

FIGS. 1A and 1B show a simplified schematic view of a biosensor apparatus 20 for detecting a binding event between a ligand and a ligand-binding receptor, in accordance with the invention. The apparatus includes a reaction chamber 22 defined in part by a substrate 24 which has a biosensor surface 26 within the chamber.

The biosensor surface has attached thereto, two-subunit heterodimer complexes, such as complexes 28, each complex carrying a ligand, such as ligands 30, which forms one of the two binding pairs of a ligand/anti-ligand agent whose binding serves as the "trigger" of a measurable biosensor event, as will be described below. FIG. 1B shows the condition of the biosensor surface after binding of ligand-binding agent, such as indicated at 34, to a portion of the ligands on the biosensor surface.

According to an important feature of the invention, each heterodimer complex, such as complex 28, includes a first peptide subunit, such as subunit 28a, which is attached to the biosensor surface, e.g., by covalent attachment, and a second, preferably oppositely charged subunit, such as subunit 28b, to which the ligand is attached. The two peptides are constructed, as will be detailed below, for self-assembly into stable, two-subunit alpha-helix coiled-coil heterodimer complexes, and when so assembled, serve to anchor the ligand on the biosensor surface as shown.

The chamber includes at least one port or opening 32 for introducing a solution or suspension into the chamber. Where the biosensor has a closed chamber, as here, the chamber may additionally include a vent or outlet port. The analyte introduced into the chamber, i.e., the compound or material to be assayed, will be either an anti-ligand binding agent, or a ligand or ligand analog which is capable of competing with surface-bound ligand for binding to a ligand-binding agent. The analyte—i.e., the ligand, ligand analog or anti-ligand agent— may be in free molecule form or may be part of a complex, e.g., a cell or macromolecular complex. Where the analyte is a ligand or ligand analog, the apparatus further includes a ligand-binding agent which may be introduced with the analyte or may be present in the chamber, e.g., immobilized on the chamber walls or present in dried, unbound form within the chamber.

Figure 1B:
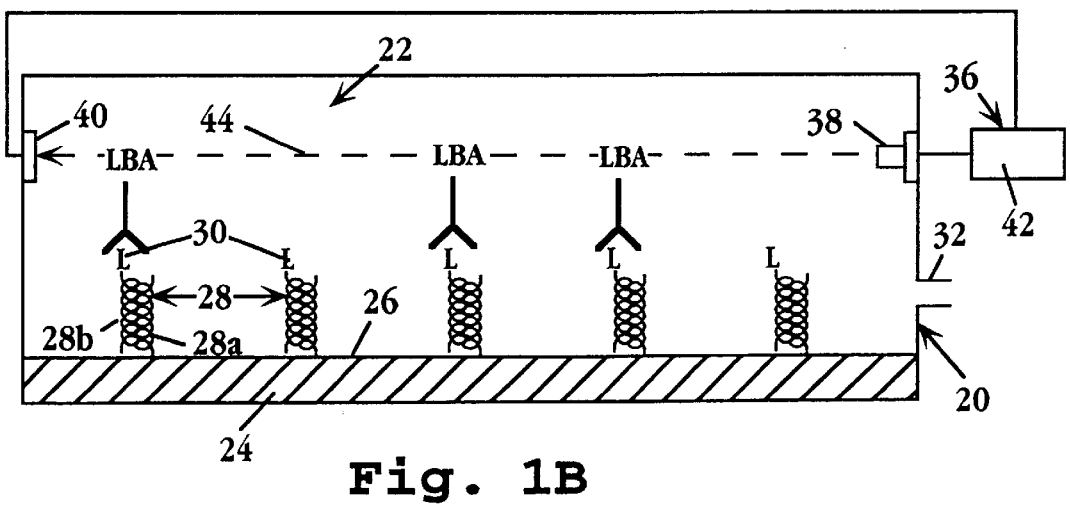

The biosensor apparatus also includes a detector or detector means 36 for detecting the presence and/or level or binding of ligand binding agent to the surface ligands. A variety of detectors are described below. For simplicity, the detector in FIG. 1 is illustrated schematically, and includes a beam source 38 for producing a beam 44, a beam detector 40, and a control unit 42 operatively connected to the beam source and detector for measuring changes in the beam, e.g., beam intensity, in response to binding of ligand-binding agent to surface-bound ligand, as illustrated in FIG. 1B.

A. Heterodimer Subunit Peptides

The heterodimer-subunit peptides employed in the biosensor invention are two non-identical, preferably oppositely charged polypeptide chains, typically each about 21 to about 70 residues in length, having an amino acid sequence compatible with their formation into two-stranded α-helical heterodimer coiled-coils. They are designated herein as HSP1 (heterodimer-subunit peptide 1), and HSP2 (heterodimer-subunit peptide 2). In the discussion below, HSP1 will refer to the peptide attached to the biosensor surface in the biosensor, and HSP2, to the peptide having an attached ligand. It will be understood that these designations refer to the functional role played by the subunit peptide, not the actual peptide sequence.

In aqueous medium, the isolated heterodimer-subunit peptides are typically random coils. When HSP1 and HSP2 are mixed together under conditions favoring the formation of α-helical coiled-coil heterodimers, they interact to form a two-subunit α-helical coiled-coil heterodimeric complex.

Peptides in an α-helical coiled-coil conformation interact with one another in a characteristic manner that is determined by the primary sequence of each peptide: The tertiary structure of an α-helix is such that 7 amino acid residues in the primary sequence correspond to approximately 2 turns of the α-helix. Accordingly, a primary amino acid sequence giving rise to an α-helical conformation may be broken down into units of 7 residues each, termed heptads. The heterodimer-subunit peptides are composed of a series of heptads in tandem. When the sequence of a heptad is repeated in a particular heterodimer-subunit peptide, the heptad may be referred to as a "heptad repeat", or simply "repeat".

Specific types of amino acid residues at defined positions in each heptad act to stabilize the two-stranded α-helical coiled-coil heterodimeric structure or complex. The heterodimer peptides may also contain residues that can be reacted (either intra- or inter-helically) to stabilize the α-helical or coiled-coil nature of the polypeptides. One example of a stabilizing modification is the incorporation of lactam bridges in the first and last (terminal) repeats of heterodimer-subunit peptides, as detailed in PCT application WO CA95/00293 for "Heterodimer Polypeptide Immunogen Carrier Composition and Method", publication date Nov. 23, 1995, which is incorporated herein by reference.

Figure 2A:
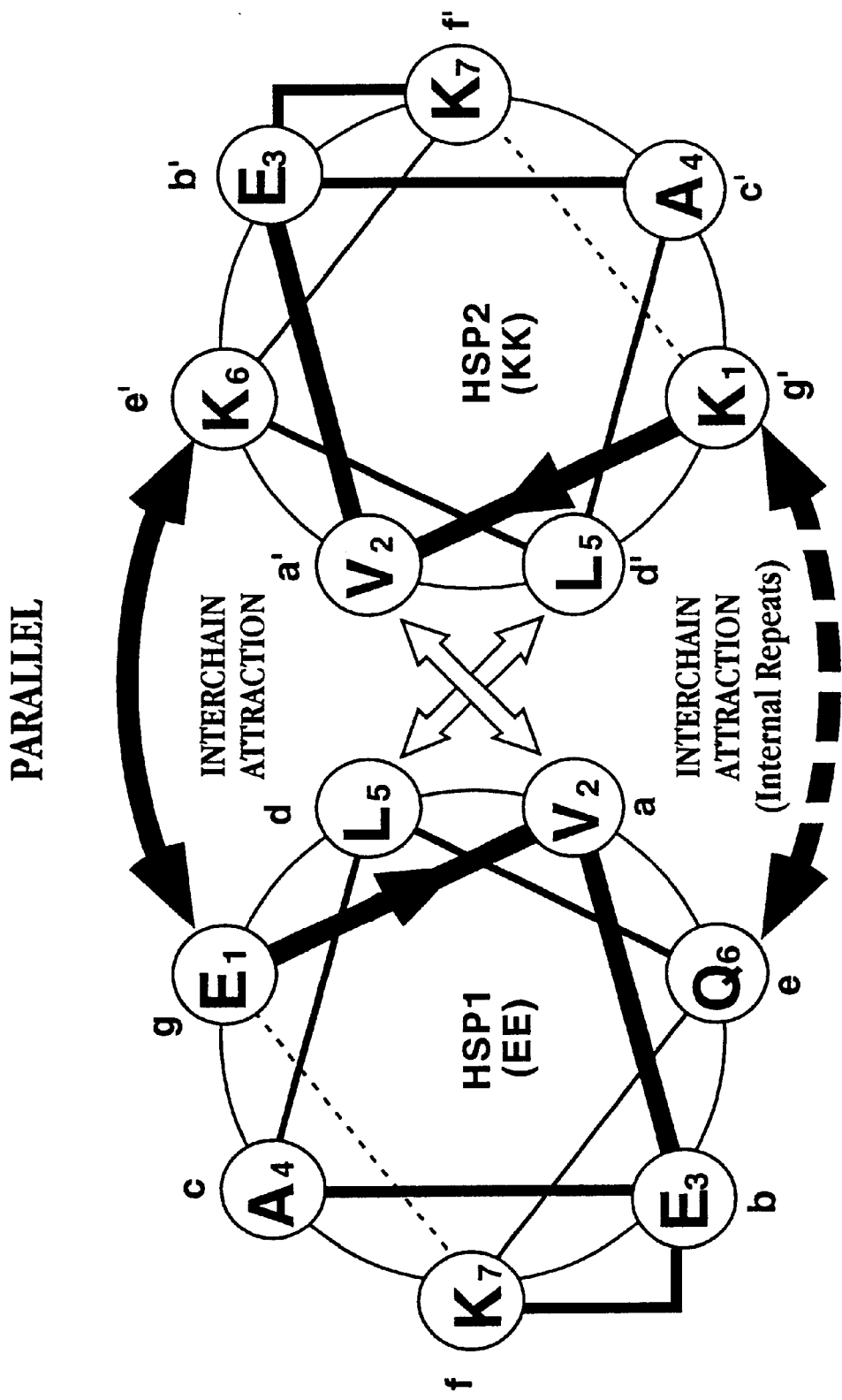
FIGS. 2A–2C show helical wheel representations of (2A) terminal heptads of two exemplary heterodimer-subunit peptides in a parallel α-helical heterodimer configuration; (2B) terminal heptads of two exemplary heterodimer-subunit peptides in an antiparallel α-helical heterodimer configuration; and (2C) helical wheel representations of specific peptides in an α-helical heterodimer configuration.
Figure 2B:
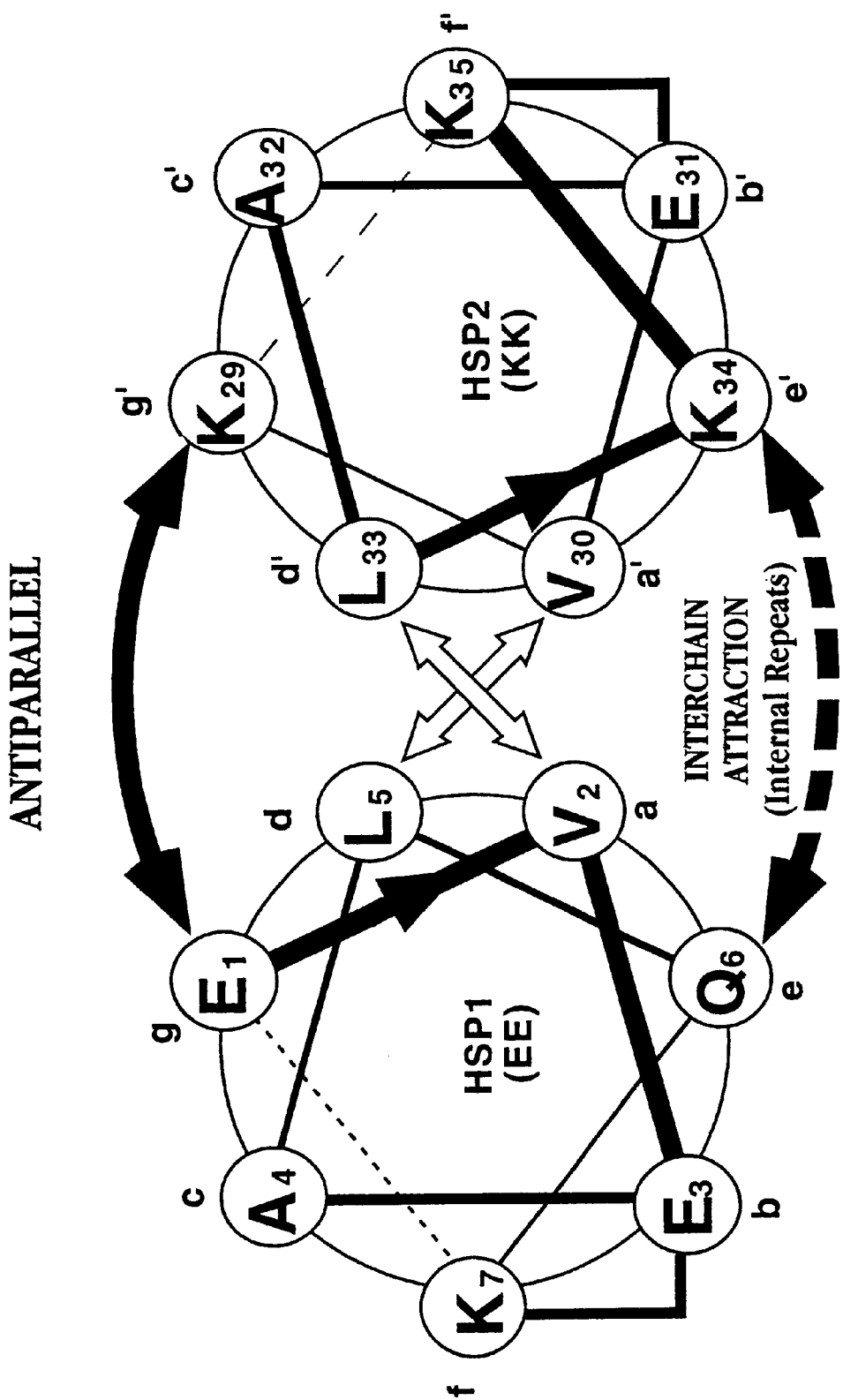

The dimerization of HSP1 and HSP2 is due to the presence of a repeated heptad motif of conserved amino acid residues in each peptide's primary amino acid sequence. The individual positions in each heptad are designated by the letters a through g for HSP1, and a' through g' for HSP2, as shown in FIGS. 2A and 2B. Repeating heptad motifs having appropriate amino acid sequences direct the HSP1 and HSP2 polypeptides to assemble into a heterodimeric α-helical coiled-coil structure under permissible conditions. The individual α-helical peptides contact one another along their respective hydrophobic faces, defined as the a and d positions of each heptad.

HSP1 and HSP2 may assemble into a heterodimer coiled-coil helix (coiled-coil heterodimer) in either parallel or antiparallel configurations. In a parallel configuration, the two heterodimer-subunit peptide helixes are aligned such that they have the same orientation (amino-terminal to carboxyl-terminal). In an antiparallel configuration, the helixes are arranged such that the amino-terminal end of one helix is aligned with the carboxyl-terminal end of the other helix, and vice versa.

Diagrams of the relative orientations of the a–g positions of two interacting α-helices are shown in FIGS. 2A and 2B. FIG. 2A shows an end-on schematic of the first two turns (one heptad) of two exemplary heterodimer-subunit peptides, EE and KK, arranged in a parallel configuration. FIG. 2B shows an end-on schematic of the same heterodimer-subunit peptides arranged in an antiparallel configuration.

Heterodimer-subunit peptides designed in accord with the guidance presented herein typically show a preference for assembling in a parallel orientation vs. an antiparallel orientation. For example, the exemplary peptides identified by SED ID NO:1 and SEQ ID NO:2 in the above CA95/00293 PCT patent application, form parallel-configuration heterodimers as do other peptide sequences discussed in the PCT application. When attaching a ligand to HSP2, it is generally desirable to attach the ligand at or near the end of the peptide that will form the distal end of the heterodimer. In particular, where the heterodimer forms a parallel configuration, the HSP1peptide is preferably anchored to the biosensor surface at its C terminus, and the ligand attached to the HSP2peptide at its N terminus.

Figure 2C:
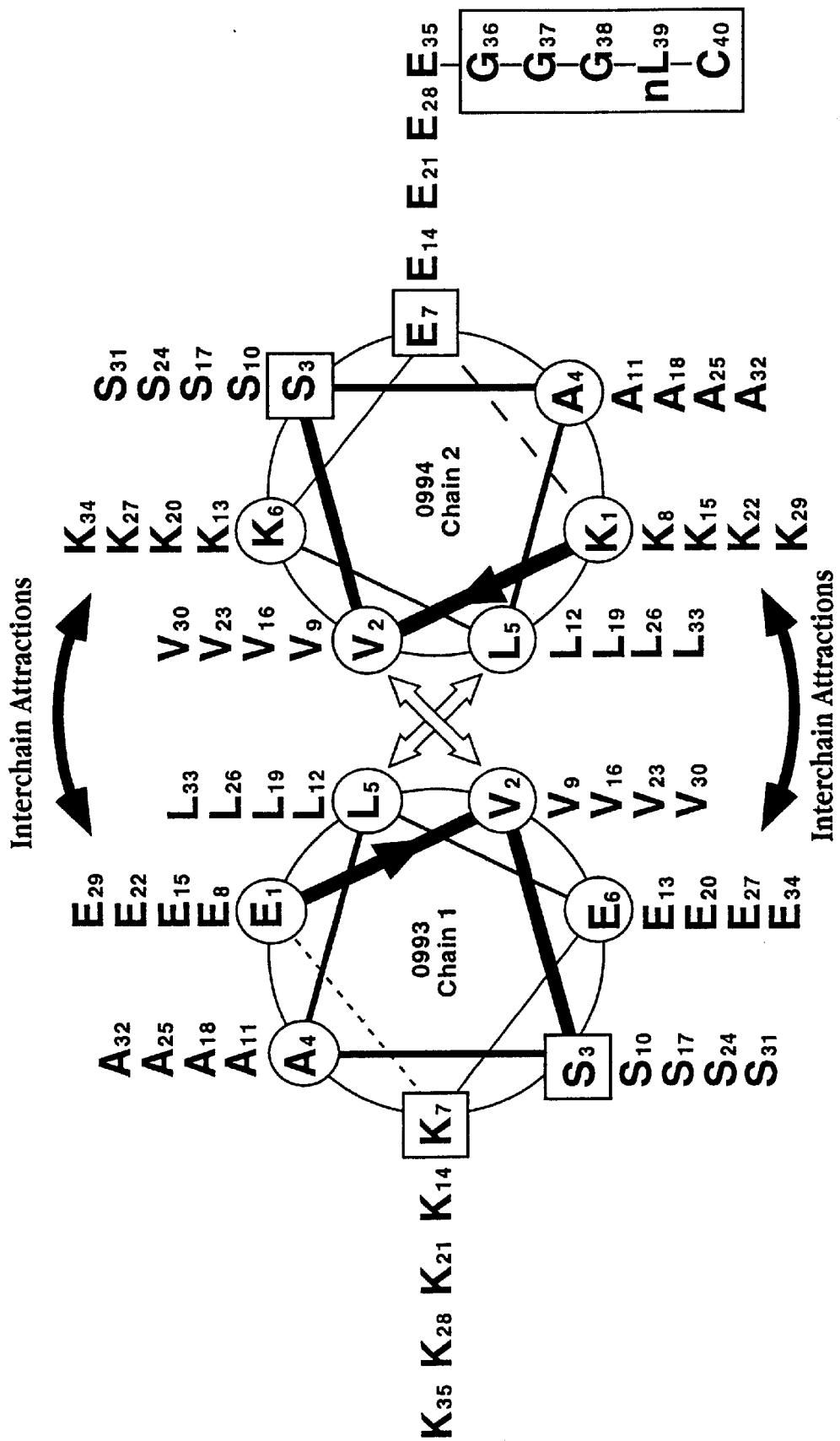

In FIGS. 2A, 2B and 2C, amino acids are circled and indicated by the one-letter code, and consecutive amino acid positions are numbered and joined by lines with arrow heads indicating the N-terminal to C-terminal direction. Interactions between the two helixes are indicated by arrows. Wide arrows crossing between the helixes depict hydrophobic interactions between the a and d positions of adjacent helixes.

Ionic interactions between the e and g positions of adjacent helixes are indicated as curving arrows above and below the nexus of the helixes. In FIGS. 2A and 2B, position e of peptide EE is a Gln in the first and last heptad, and a Glu in the internal heptads. The (bottom) curving arrow depicting ionic interactions with this position is drawn with a dashed line to indicate that ionic interactions are present between internal heptads of the helixes, but not between the first and last, or terminal, heptads. Lactam bridges in FIGS. 2A and 2B are indicated as a right-angle line between the f and b positions within each helix.

The hydrophobic interactions between the helixes are due to hydrophobic residues at the a and d positions of the heterodimer-subunit peptides. Residues at these positions, effective to maintain the helixes in contact, include leucine, isoleucine, valine, phenylalanine, methionine, tryptophan, tyrosine, alanine and derivatives of any of the above. Other residues, including alanine, cysteine, serine, threonine, asparagine and glutamine may also occupy a or d positions in some heptads, so long as others are occupied by hydrophobic residues.

Appropriate selection of the specific residues to occupy the a and d positions is important. If the hydrophobic interactions are strong, as is the case, for example, between helixes containing Ile at one of the positions and Leu at the other position, a significant fraction of the helixes will form as homodimers at pH 7, even if like-charged residues are present at the e and g positions to discourage homodimer formation. If, on the other hand, residues at the a and d positions are selected such that the hydrophobic interactions are too weak (for example, Ala at both positions), the helixes may not form coiled-coil dimers at all. Preferably, residue pairs are selected that promote the formation ≧95% heterodimers at pH 7. An exemplary pair of residues at the a and d positions, that results in hydrophobic interactions conducive to ≧95% heterodimer formation at pH 7, comprises Leu at one of the positions and Val at the other position. These residues are present at the a and d positions of exemplary heterodimer-subunit peptides.

Figure 3A:
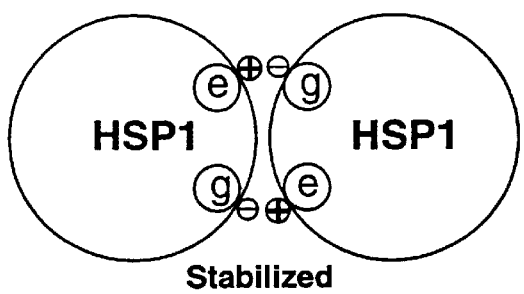
FIGS. 3A–3E show schematic representations of adjacent heptads of two heterodimer-subunit peptides in a parallel configuration comparing the stabilizing/destabilizing effects of charged residues at the e and g positions in homodimers vs. heterodimers.
Figure 3B:
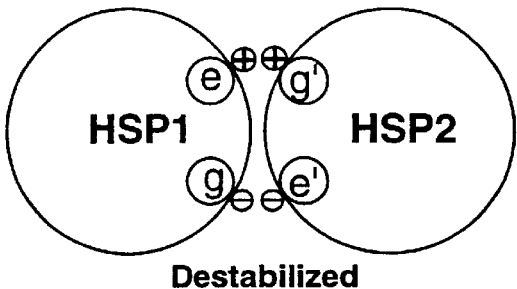
Figure 3C:
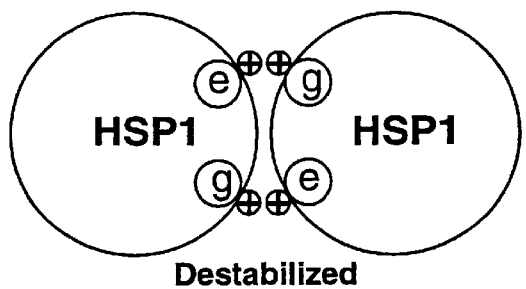
Figure 3D:
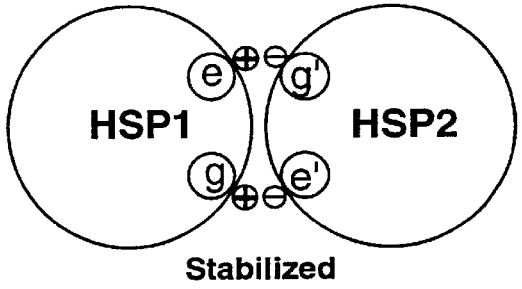
Figure 3E:
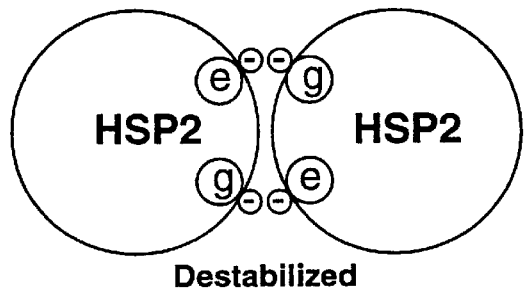

Dimeric coiled-coil conformations of α-helixes are preferably also stabilized by ionic interactions between residues at the e and g positions of adjacent helixes, as is illustrated in FIGS. 3A and 3D. If each helix of a dimer has a positively-charged residue at one position, for example, e, and a negatively-charged residue at the other position, for example, g, homodimer formation is favored (FIG. 3A; compare with heterodimer in FIG. 3B). However, if each helix has like-charged residues at both positions, then two oppositely-charged helixes will tend to associate into heterodimers (FIG. 3D), as opposed to forming homodimers (FIGS. 3C, 3E). The reader is referred to above-mentioned WO 95/31480 for exemplary heterodimer sequences and methods of synthesis.

B. Ligand Attachment to the Biosensor Surface

As noted above, one of the two subunit peptides (HSP1) in the heterodimer is attached to the biosensor surface, and the second peptide (HSP2) contains a ligand intended to participate in an analyte-dependent ligand/anti-ligand binding reaction. In both cases, the peptide is synthesized, or derivatized after synthesis, to provide the requisite attachment function and ligand, respectively.

Figure 4A:
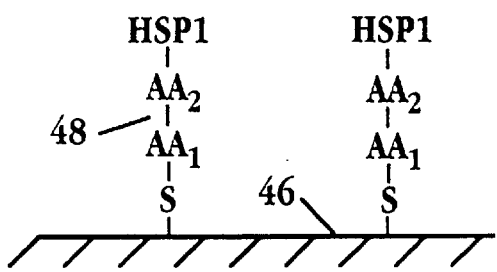
FIGS. 4A and 4B illustrate alternative methods for coupling an HSP1 subunit peptide to a biosensor surface in a biosensor.

Considering the modification of HSP1, the peptide may be synthesized, at either its N or C terminus, to carry additional terminal peptides that can function as a spacer between the biosensor surface and the helical-forming part of the peptide. FIG. 4A shows an HSP1 peptide attached to a metal, e.g, gold, surface 46 through an polypeptide spacer 48 terminating in a cysteine or methionine residue which provides for covalent coupling to the surface through a thiolate linkage, under standard conditions (e.g., Dakkouri, A.S., et al., *Langmuir* (1996) 12:2849–2852).

Figure 4B:
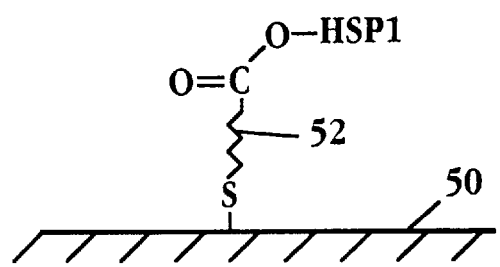
Figure 5A:
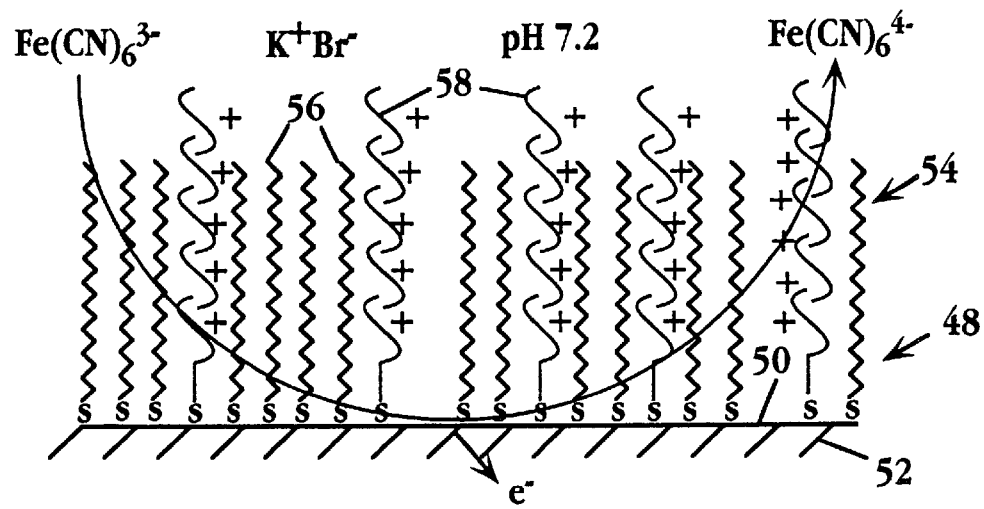
FIGS. 5A and 5B illustrate hydrocarbon-chain monolayers formed on a biosensor surface in a biosensor with an K-coil peptide alone embedded in the monolayer (5A) and a K-coil/E-coil heterodimer embedded in the monolayer (5B)
Figure 5B:
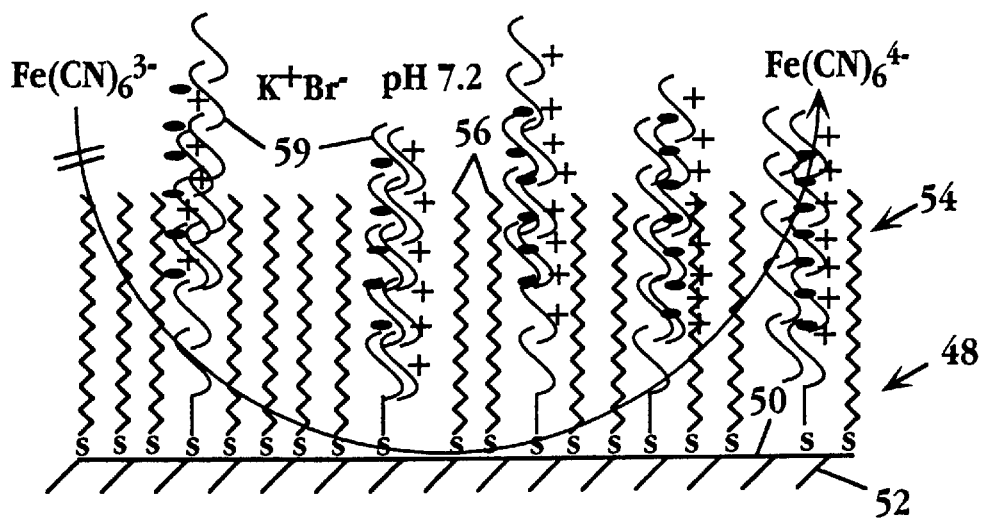
Figure 6:
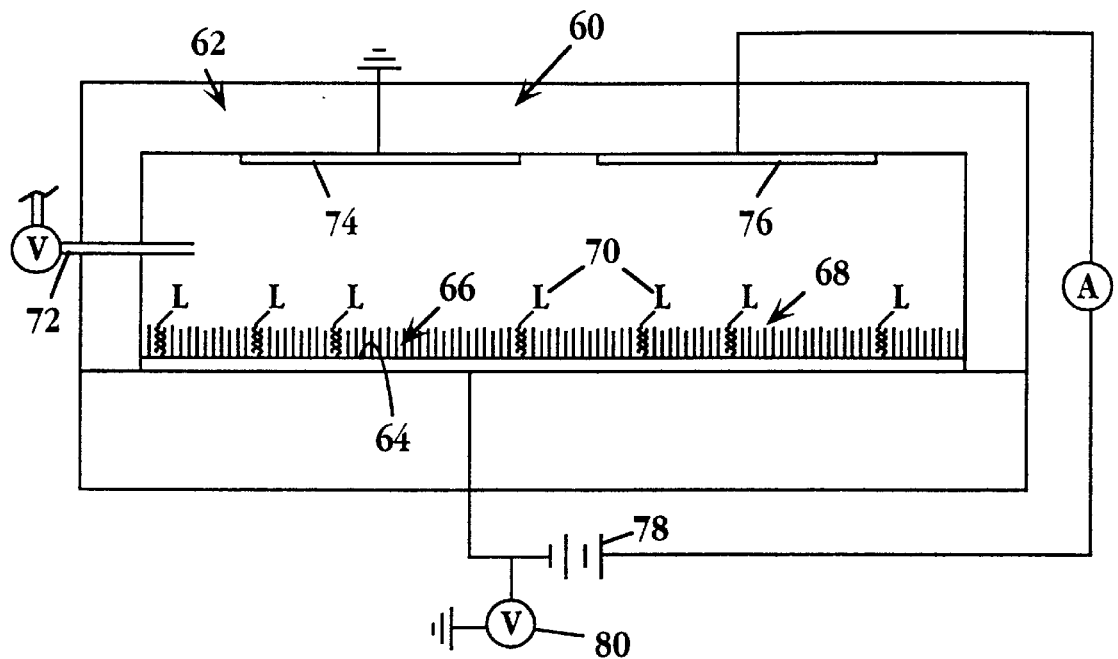
FIG. 6 shows elements of an amperometric biosensor constructed in accordance with one embodiment of the invention.

For HSP1 coupling to a glass or polymer surface, the C or N terminal residue can be derivatized with a suitable activated functional group that allows direct coupling of the peptide end to a selected amine, acid, alcohol, or aldehyde group on the surface. These groups can be introduced during solid phase synthesis according to standard methods, with other reactive side chains in the peptide being protected with suitable protecting groups. Alternatively, the HSP1 peptide can be attached to the biosensor surface thorough a high-affinity binding reaction, such as between a biotin moiety carried on the peptide and an avidin molecule covalently attached to the surface.

Where the heterodimer is embedded in a hydrocarbon-chain monolayer, as described below, the spacer anchoring the HSP1 peptide to the biosensor surface may be a hydrocarbon chain, such as spacer chain 52 anchoring HSP1 to biosensor surface 50 in FIG. 4B. The chain is preferably a fractional length of the chains making up the bilayer, such that the distal ends of the heterodimer peptides in the assembled monolayer are at or near the exposed surface of the monolayer. Thus, for example, if the monolayer is made up of 18-carbon chains, the spacer is preferably 2–10 carbons in length, depending on the length of the assembled heterodimer.

The hydrocarbon-chain spacer, in the form of a omega-thio fatty acid, may be coupled to a terminal hydroxyl or amine coupling during solid-phase synthesis, as outlined above. The derivatized peptide, in turn, can be attached to a metal surface by standard thiolate coupling (Dakkouri, supra).

Considering the ligand-attachment to HSP2, the ligand selected will be determined by the analyte to be tested. Ligand-receptor binding pairs, i.e., ligand/ligand-binding agent pairs used commonly in diagnostics include antigen-antibody, hormone-receptor, drug-receptor, cell surface antigen-lectin, biotin-avidin, substrate/enzyme, and complementary nucleic acid strands. The ligand is typically the smaller of the two binding pair members, particularly where the ligand is attached to a hydrocarbon-chain monolayer, as described below. However, attachment of either binding pair is contemplated herein.

Where the ligand is a polypeptide, e.g., peptide antigen, the antigen can be synthesized by either solid-state or recombinant methods, to include the peptide antigen at the end of the HSP2 peptide that will orient distally in the assembled heterodimer. Where the ligand is a non-peptide moiety, e.g., a non-peptide hormone, drug, or nucleic acid, the HSP2 peptide can be synthesized to include one or more residues that can be specifically derivatized with the ligand. The ligand is preferably covalently attached to an aminoacid coupling residues at positions b, c and/or f of one or more heptads in HSP2 (FIG. 2A). These positions lie along the outward face of a coiled-coil heterodimer. In an exemplary embodiment, a single coupling residue is placed at the f position of a terminal heptad of HSP2, or at the terminal residue. This residue may be derivatized during solid-state synthesis according to known methods, allowing selective deprotection of the residue to be reacted.

Preferred coupling groups are the thiol groups of cysteine residues, which are easily modified by standard methods. Other useful coupling groups include the thioester of methionine, the imidazolyl group of histidine, the guanidinyl group of arginine, the phenolic group of tyrosine and the indolyl group of tryptophan. These coupling groups can be derivatized using reaction conditions known to those skilled in the art.

To attach the ligand-derivatized HSP2 peptide to the surface-immobilized HSP1 peptide, the two peptides are contacted under conditions that favor heterodimer formation. A medium favoring coiled-coil heterodimer formation is a physiologically-compatible aqueous solution typically having a pH of between about 6 and about 8 and a salt concentration of between about 50 mM and about 500 mM. Preferably, the salt concentration is between about 100 mM and about 200 mM. An exemplary benign medium has the following composition: 50 mM potassium phosphate, 100 mM KCl, pH 7. Equally effective media may be made by substituting, for example, sodium phosphate for potassium phosphate and/or NaCl for KCl. Heterodimers may form under conditions outside the above pH and salt range, medium, but some of the molecular interactions and relative stability of heterodimers vs. homodimers may differ from characteristics detailed above. For example, ionic interactions between the e and g positions that tend to stabilize heterodimers may break down at low or high pH values due to the protonation of, for example, Glu side chains at acidic pH, or the deprotonation of, for example, Lys side chains at basic pH. Such effects of low and high pH values on coiled-coil heterodimer formation may be overcome, however, by increasing salt concentration.

Increasing the salt concentration can neutralize the stabilizing ionic attractions or suppress the destabilizing ionic repulsions. Certain salts have greater efficacy at neutralizing the ionic interactions. For example, in the case of the K-coil peptide in FIG. 2A, a 1M or greater concentration of $ClO_4^-$ anions is required to induce maximal α-helical structure (as determined by CD measurements performed as detailed in Example 2), whereas a 3M or greater concentration of $Cl^-$ ions is required for the same effect. The effects of high salt on coiled-coil formation at low and high pH also show that interhelical ionic attractions are not essential for helix formation, but rather, control whether a coiled-coil tends to form as a heterodimer vs. a homodimer.

C. Biosensor Surface with Hydrocarbon-Chain Monolayer

In one preferred embodiment, for use in a variety of the biosensors described below, the biosensor surface is modified to contain a hydrocarbon-chain monolayer, as illustrated in FIGS. 5A and 5B. The figures are enlarged views of a portion of a biosensor surface 48, including a thin electrode film 50 on a substrate 52, and a monolayer 54 formed of hydrocarbon chains, such as chains 56, attached to the film through thioether linkages. Embedded in the monolayer are molecules of the HSP1 peptide, such as molecules 58 (FIG. 5A, before addition of HSP2 peptide), anchored to the surface as described above, and heterodimer complexes, such as complexes 59 (FIG. 5B, after addition of HSP2 peptides).

The chains forming the monolayer are typically 8–22 carbon, saturated hydrocarbon chains, although longer chains, chains with some unsaturation, chains with non-carbon chain atoms, such as lipid ethers, and/or chains with minor branching, such as by nonchain methyl groups, may be employed. In an amperometric biosensor embodiment, to be described below, the chains are sufficiently close packed and ordered to form an effective a barrier to electron transfer flow, under biosensor operating conditions, as discussed below. This density is calculated to be between 3–5 chains/$nm^2$.

With reference to FIG. 5A, the HSP1 peptide is included in the monolayer in a mole ratio peptide/hydrocarbon chains of preferably between 1:100 to 1:5. As indicated in the figure, and discussed below, the FIG. 5A monolayer is leaky to ion carriers, such as $Fe(CN)_6^{3-}$, and as a result, gives a measurable detector current in the absence of analyte. The leakiness of the membrane is presumably due to the disruption of the monolayer by charge-charge repulsion between the charged peptides in the monolayer, as shown, and a diminution of the electrostatic potential barrier in the monolayer.

With reference to FIG. 5B, addition of an oppositely charged HSP2 peptide neutralizes the HSP1 peptide charges, with the result that the membrane assumes a low conductance property, as evidenced by substantially reduced current in the presence of charge carriers. This property of the biosensor surface will be described further below with respect to FIGS. 7–9.

In a preferred method for forming the monolayer, a mixture of thiol-containing chains and thiol-terminated HSP1 peptide, at a selected mole ratio, is actively driven to the surface by applying a positive voltage potential to the substrate surface, e.g., gold film. In practice, the hydrocarbon chain mixture (about 1 mM hydrocarbon chains) in an ethanolic solution of 100 mM Li perchlorate, neutral pH, is placed over the electrode, and a selected potential is applied to the electrode. The buildup of the monolayer can be monitored by increase in layer thickness. Alternatively, monolayer formation is monitored by measuring current across the monolayer, as described below. In this case, formation of the monolayer will be characterized by a steady drop in electrode current, until minimum current is reached, at which point maximum chain packing has been achieved.

The time required to achieve saturation packing density will vary with applied voltage, and can be as short as 10 seconds—about 4 orders of magnitude faster than monolayer formation by diffusion. Complete or nearly complete monolayer formation (30 Å thickness) occurs within 10 minutes at about 1V potential and above. At lower positive voltages, additional reaction time is required. Preferably the voltage applied to the electrode is at least between about +250 mV relative to a normal hydrogen electrode (+250 vs. NHE) and 1.2V (vs. NHE).

Not only are rapid monolayer formation times achieved, but the percentages of peptide and hydrocarbon chains present in the reaction mixture are precisely represented in the monolayers, giving highly reproducible electrode characteristics.

To complete formation of the monolayer with attached ligand, the ligand-derivatized HSP2 peptide is contacted with the monolayer under conditions favoring heterodimer formation, as detailed above, where the HSP2 peptide is preferably added in excess. The formation of heterodimers can be followed by measuring current across the monolayer. Because heterodimer formation tends to "tighten" the monolayer, as discussed above, heterodimer formation will lead to a steady drop in measured electrode current, until a stable low current is reached, at which point maximum heterodimer formation has occurred.

The subsections below illustrate several types of biosensors for which the biosensor surfaces described above are suitable.

D. Amperometric Biosensor

FIG. 6 illustrates, in simplified view, elements of an amperometric biosensor 60 constructed in accordance with one embodiment of the invention. The apparatus has a closed chamber 62 housing a biosensor surface 64 formed of a gold film 66, which forms the surface electrode in the biosensor. The electrode surface is covered by a monolayer 66 of hydrocarbon chains which define an exposed monolayer surface 68. The monolayer includes ligand-bearing heterodimers, such as indicated at 70, embedded therein, with the ligands disposed at or near the monolayer surface, for accessibility to reaction with ligand-binding agents. The monolayer is formed as above, e.g., with thioether attachment of monolayer components to the gold film.

The biosensor chamber serves to hold an aqueous electrolyte solution required for biosensor operation, as will be described. Liquid may be introduced into or withdrawn from the chamber through a valved port 72, and chamber may include a second port or vent (not shown) to facilitate liquid flow through the port.

A reference electrode 74 and a counter electrode 76 in the apparatus are carried on the upper chamber wall, as shown, and are both in conductive contact with electrode 64 when the chamber is filled with electrolyte solution. The reference electrode, which is held at ground, serves as the voltage potential reference of the working electrode, when a selected potential is placed on the working electrode by a voltage source 78. This potential is measured by a voltage measuring device 80 which may additionally include conventional circuitry for maintaining the potential at a selected voltage, typically between about −500 to +800 mV.

Voltage source 78 is connected to counter electrode 76 through a current measuring device 82 as shown, for measuring current between the two electrodes during biosensor operation. The reference and counter electrodes are Pt, Ag, Ag/AgCl, or other suitable electrodes. The reference and working electrodes, and the circuitry connecting them to the working electrode, are also referred to herein, collectively, as detector means for measuring ion-mediated current across the working-electrode monolayer, in response to ligand-receptor binding events occurring at the monolayer surface.

In operation, the chamber is filled with a solution containing analyte and ionic species capable of undergoing a redox reaction, i.e., losing or gaining an electron, at a suitably charged electrode. Exemplary redox species are $Fe(CN)_6^{3-/4-}$, as a negatively charged species, and $Ru(NH_3)_6^{2+/3+}$ as a positively charged species. Other probes which can be used include $Mo(CN)_6^{3-}$ ($E_0$=+800 mV), $W(CN)_6^{3-}$ ($E_0$=+580 mV), $Fe(CN)_4^{-}$ ($E_0$=+580 mV), $Ce^{4+/3+}$ ($E_0$32 +1.4V), and $Fe^{+3/2+}$ ($E_0$=+666 mV). Typical redox ion concentrations are between 0.01 and 10 mM. The redox solution is contained in chamber and is in contact with reference and counter electrodes.

The voltage potential placed on the electrode, i.e., between the electrode and reference electrode, is typically at least 90 mV above the electrochemical potential ($E_0$) value of the redox species, for oxidation, and at least 90 mV below the electrochemical potential, for reduction of the species. Consider, for example, $Fe(CN)_6^{3-/4-}$, with an $E_0$ of 450 mV (vs. NHE). Above about 550 mV electrode potential, any Fe2+ species is oxidized to Fe3+, and at an electrode potential below about 350 mV, and Fe+3 is reduced to Fe+2. Similarly, $Ru(NH_3)_6^{2+/3+}$ has an $E_0$ of +50 mV (vs. NHE), so oxidation is achieved at an electrode potential above about +150 mV, and reduction, below about −50 mV.

The ability of heterodimer formation in the monolayer to enhance the close packed structure of the monolayer, as evidenced by monolayer conductance, is illustrated in FIG. 7. The figure shows the drop in conductance, as measured by ion-mediated current flow, after addition to a monolayer containing a K-coil peptide alone, of an oppositely charged E-coil peptide. The pairing of the two peptides to form charge-neutral heterodimers in the monolayer is effective to reduce monolayer conductance substantially, as evidenced by the time-dependent fall in measured oxidation or reduction current in the presence of $Fe(CN)_6^{3-}$ ions.

In one exemplary biosensor, the biosensor surface includes (i) a monolayer with embedded K-coil peptides (HSP1) covalently attached to the electrode surface, (ii) oppositely charged E-coil peptides (HSP2) forming heterodimers with the K-coil peptides in the monolayer, and (iii) surface disaccharide ligands derivatized to the E-coil peptides and disposed therefore at the monolayer surface. As seen in FIG. 8, addition of the anti-ligand receptor (a PAK protein receptor) produces an increase in both oxidation and reduction currents, with the current increase over time reflecting the kinetics of receptor binding to the surface ligands.

A similar biosensor having a trisaccharide, rather than disaccharide, ligand attached to the E-coil peptide subunit in the electrode monolayer was tested with a Verotoxin receptor, with the results seen in FIG. 9. The solid lines in the figure show the increase in oxidation and reduction current observed, as a function of time, after addition of Verotoxin.

In the absence of receptor binding to the ligand, the monolayer retains its dense ordered packing, forming an effective barrier to current across the monolayer mediated by the redox ion species, when a suitable oxidizing or reducing potential is placed across the monolayer. This is reflected by a low or zero measured current across the membrane. The dielectric constant of the monolayer in this condition is typically about 1–2.

The triggering event in the biosensor is the binding of a ligand-binding agent to the surface-bound ligand. This binding perturbs the ordered structure of the monolayer sufficiently to allow the movement of redox species through the monolayer, producing current through the electrode. Measurements performed in support of the invention indicate that one triggering event leads to $10^2$ to $10^6$ ionic and electron transfer events per second, and thus is highly multiplicative. The biosensor records this binding event as an increase in current across the electrode, i.e., between the working and counter electrodes.

By analogy to a transistor, the redox solution serves as the "source", the monolayer as the "gate", and the underlying electrode as the "drain". Current in a transistor is initiated by applying a threshold voltage to the gate. In the biosensor of the invention, current is initiated by a stimulus—in this case, a ligand-receptor binding event—to the monolayer "gate".

E. Gravimetric Biosensor

Figure 10:
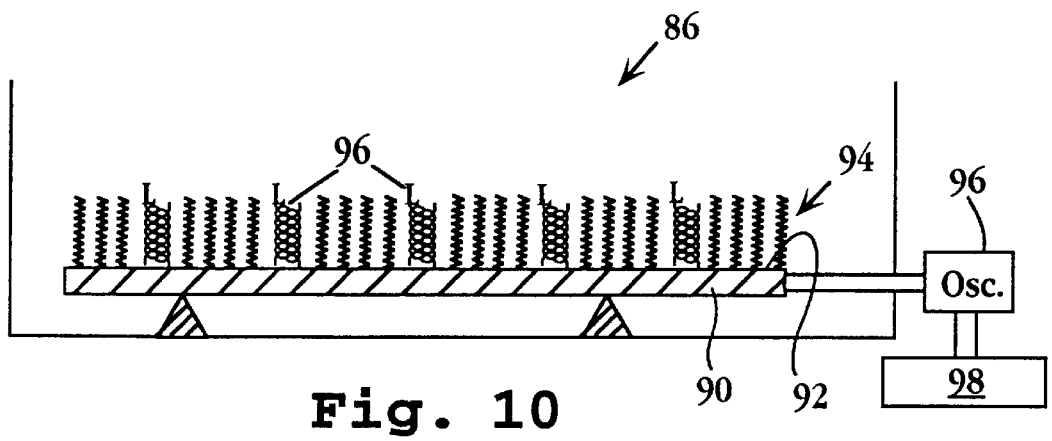
FIG. 10 shows elements of a gravimetric biosensor constructed in accordance with an embodiment of the invention.

FIG. 10 shows basic elements of a gravimetric biosensor 86 incorporating the novel biosensor surface of the invention. The biosensor has a piezoelectric crystal 90 whose biosensor surface 92 includes a monolayer 94 with ligand-bearing heterodimer complexes, such as complex 96, embedded therein.

Surface acoustic waves (SAW) are generated in the crystal by an oscillator 96. According to known piezoelectric biosensor principles, the change in mass in the biosensor surface resulting from the binding of ligand-binding agent to the surface-bound ligand alters the frequency, resonance frequency, and wavelength of the SAW, and at least one of these wave characteristics is measured by a detector 98. The oscillator and detector collectively form detector means for detecting binding of ligand-binding agent to the biosensor surface. Details of crystal construction and associated detector means in gravimetric biosensors are given, for example, in U.S. Pat. Nos. 5,478,756 and 4,789,804, and in PCT application WO 96/02830.

F. Surface Plasmon Resonance Biosensor

Figure 11:
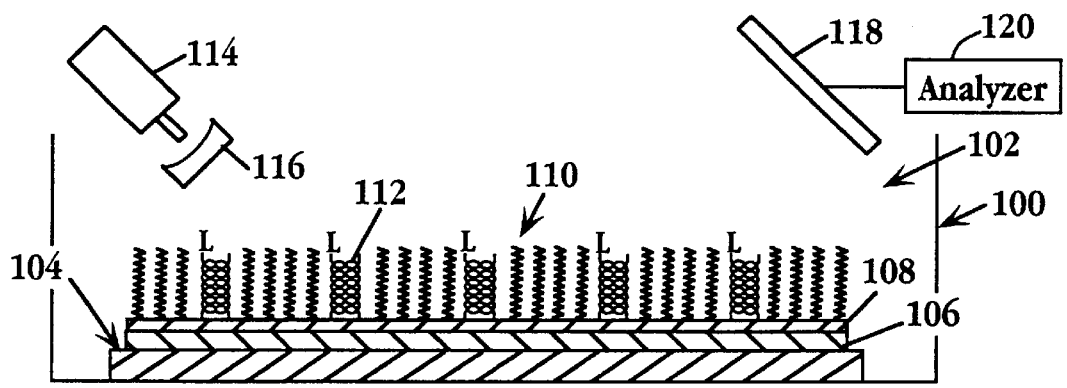
FIG. 11 shows elements of a surface plasmon resonance biosensor constructed in accordance with an embodiment of the invention.

FIG. 11 shows basic elements of a surface plasmon resonance (SPR) biosensor 100 incorporating the novel biosensor surface of the invention. An open-top chamber 102 in the biosensor contains a waveguide 104 composed of a dielectric film 106 and a thin evaporated metal film 108 constructed to support surface plasmon waves at the dielectric/metal film interface. The waveguide surface forms a biosensor surface having a monolayer 110 with ligand-bearing heterodimer complexes, such as complex 112, embedded therein.

A light source 114 direct a divergent light beam onto the biosensor surface through a lens 116. At some region along the length of the biosensor surface, the beam angle strikes the surface at an absorption angle at which absorption from the evanescent wave by surface plasmons occurs. The absorption angle will shift with changes in the composition of the material near the interface, that is, in response to binding events occuring on the monolayer surface.

The intensity of reflected light from each region along the biosensor surface is monitored by a photosensor 118 whose photosensing grid is matched to specific detector surface regions, and which is operatively connected to an analyzer 120. The light source and photosensor are also referred to herein as biosensor means.

In operation, the SPR absorption angle on the biosensor surface is measured before and after analyte addition, with the measured shift in angle being proportional to the extent of surface ligand binding to ligand-binding agent.

G. Optical Biosensor

Figure 12:
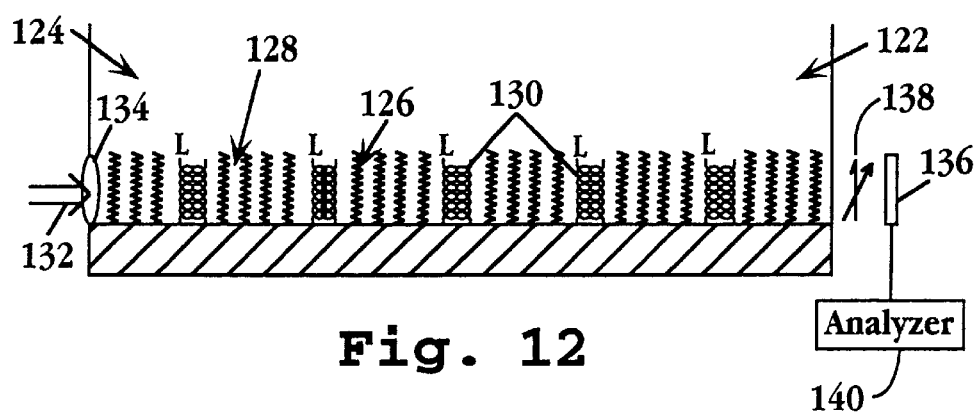
FIG. 12 shows elements of an optical biosensor constructed in accordance with an embodiment of the invention.

A variety of biosensor devices which rely on changes in the optical properties of a biosensor surface, in response to ligand/anti-ligand binding events, have been proposed. FIG. 12 shows basic elements of an optical biosensor apparatus 122 having an open chamber 124 and a biosensor surface 126 which includes a hydrocarbon-chain monolayer 128 with embedded heterodimer complexes, such as shown at 130.

The detector means in the apparatus for detecting binding events on the biosensor surface includes a source 132 of polarized light and a lens system 134 for directing the light in a beam through the region of the monolayer. A photodetector 136 at the opposite side of the biosensor surface functions to measure intensity of light at a given polarization angle, through a polarization filter 138. Detection of ligand binding events is based on the change of polarization angle and intensity of light transmitted by the monolayer in response to perturbation of the regular order of the monolayer by surface binding events. These changes are recorded by an analyser 140 operatively connected to the photosensor.

The biosensors described above have single-region biosensor surfaces, i.e., biosensor surfaces containing a single ligand, for use in detecting a single analyte. These surface are readily constructed, as discussed above, by contacting a selected HSP2-ligand conjugate with a universal HSP1 biosensor surface, then adding the desired HSP2-ligand conjugate under conditions of heterodimer formation.

It will be appreciated that the method of the invention can be used to construct a biosensor with multiple sensor surfaces, or to partition a single surface into several different-ligand regions, for carrying out multi-analyte tests. In the latter embodiment, different HSP2-ligand conjugates are contacted with the different selected regions on a universal sensor surface. The present invention allows for flexibility in terms of number and types of ligands attached, after manufacture of the biosensor surface(s), particularly where the distinct biosensor regions can be selectively contacted with different HSP2-ligand conjugates.

The next section describes a more general method in accordance with the invention for forming a biosensor surface with multi-reagent regions, for use particularly in constructing a biosensor surface with a high density of different ligand-containing test regions.

II. Producing a Multi-Ligand Surface

Figure 13A:
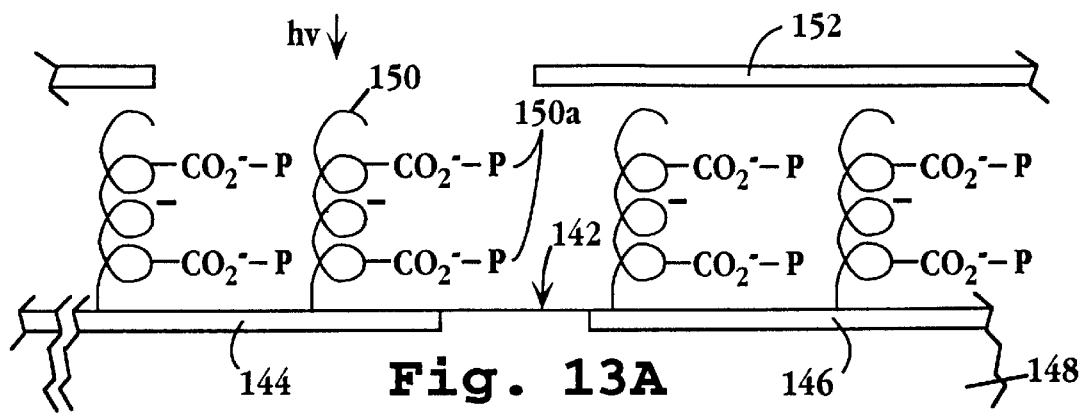
FIGS. 13A–13C illustrate steps in the attachment of an assay reagent to an irradiated region of a biosensor surface, in accordance with a method of the invention.
Figure 13B:
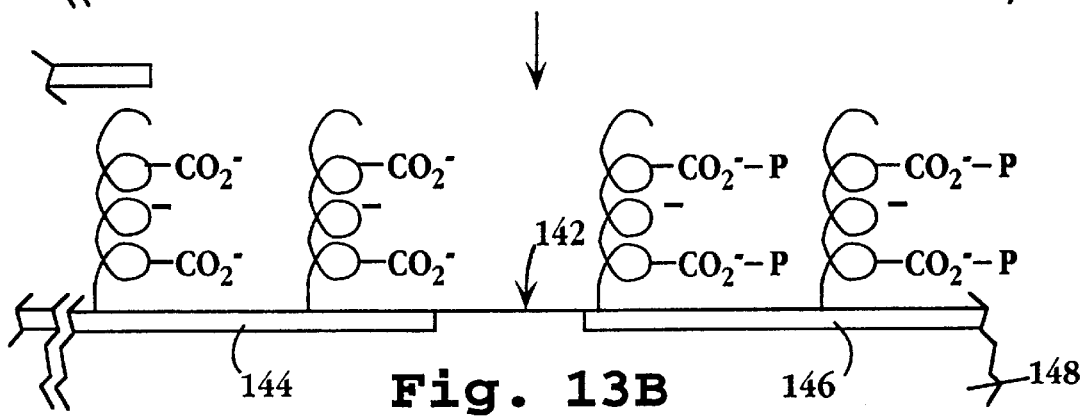
Figure 13C:
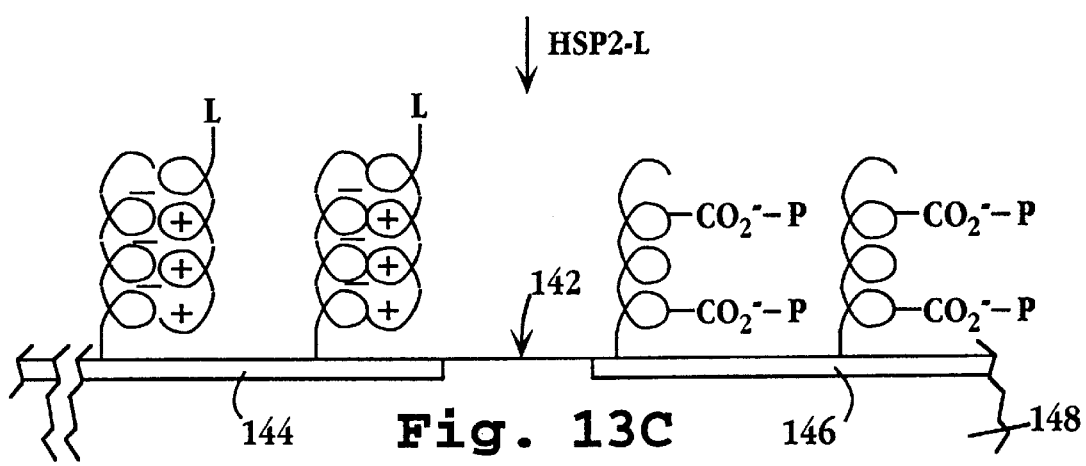

FIGS. 13A–13C illustrate the first iteration in a method of constructing an array of different biological reagents in different, selected regions on an assay support surface, in accordance with the invention.

FIG. 13A shows a portion of an assay support surface 142—in this case, a biosensor surface for use in an amperometric biosensor device. The surface has been constructed, e.g., by conventional photolithographic methods, to include an array of electrode regions, such as the two regions 144, 146. In the embodiment illustrated, the regions are metal, e.g., gold, film region formed on a substrate 148. Although not shown here, the surfaces are prepared as above as hydrocarbon-chain monolayers with HSP1 peptides, such as shown at 150, embedded in the monolayer.

According to an important feature of the invention, the HSP1 peptides have one or more photo-releasable blocking groups, such as blocking groups 150a on peptide 150, that prevent heterodimer formation in the presence of HSP2 peptide under selected conditions. In the present case, the HSP1 peptide is an E-coil peptide, and the blocking groups are nitrophenolate protecting groups on two or more of the glutamate side chain carboxyl groups. Those skilled in the art will recognize that a variety of photo-releasable blocking groups, e.g., various photo-deprotectable groups on one or more of amino acid side chains, can be used to block heterodimer formation, either by steric interference or by reducing charge interactions.

Following attachment of the HSP1 peptide with blocking groups to the assay surface, or as part of a monolayer on the surface, the surface is selectively irradiated to release blocking groups in irradiated regions of the surface only. This can be accomplished, as illustrated in FIG. 13A, by irradiating the surface through a photomask 152 placed over the surface, to selectively irradiate regions of the surface corresponding to photomask openings. FIG. 13B shows selective release of blocking groups from the irradiated region 144.

The surface is then reacted with an HSP2 peptide 154 (FIG. 13C) conjugated to a selected ligand, as shown, to form heterodimers selectively in the unblocked regions of the surface. If necessary, the heterodimer formation conditions are selected, e.g., in ionic strength, to heterodimer formation with unblocked HSP1 peptides only. Thus, if the released blocking groups expose ionic groups, e.g., carboxyl groups, it may be useful to lower the ionic strength of the reaction medium, to enhance ionic interaction effects leading to heterodimer formation. The above steps are repeated for each ligand to be added to the assay surface, until the desired array of different ligands at different addressable regions of the surface is constructed.

Figure 14:
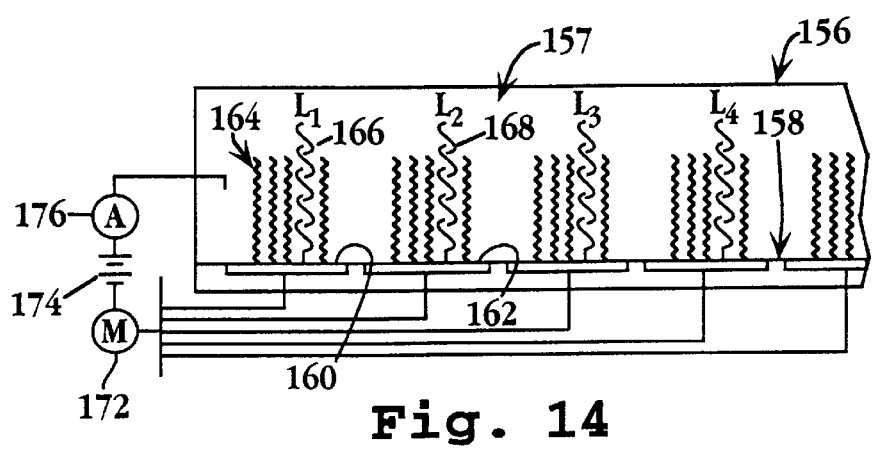
FIG. 14 is a cross-sectional view of a portion of a multi-test amperometric biosensor constructed in accordance with an embodiment of the invention.

FIG. 14 shows a portion of an multi-analyte assay surface constructed according to the above method, and employed in an amperometric biosensor apparatus 156 of the type described above. A biosensor surface 158 in a chamber 157 has a plurality of independent sensor regions, such as regions 160, 162, each having a separate ligand, such as indicated at $L_1$, $L_2$, attached to the respective sensor region through heterodimers, such as heterodimers 166 ($L_1$) and 168 ($L_2$). The heterodimers are embedded in a monolayer on each region, such as monolayer 154, for detection of different analytes in a analyte-containing sample introduced into the biosensor chamber.

Current flow in each detector region, such as regions 160, 162 is interrogated by a multiplexer 172 which connects each region to the chamber reservoir through a voltage source 174 and current device 176. As above, binding of ligand-binding agent to any region will perturb the monolayer structure of that region, causing a measured current increase in the region(s) where such binding has occurred.

From the foregoing, it can be seen how various objects and advantages of the invention are met. The biosensor surface of the invention can be formed under controlled manufacturing conditions consistent with microchip scale and photomask processes, to produce highly uniform and/or miniaturized and/or high-density array sensor devices with attached HSP1 peptides.

After manufacture of a device with a universal surface, the sensor surface can be readily adapted to a wide variety of ligand(s), by reacting the sensor surface with the an HSP2 peptide derivatized with the selected ligand. The ligand-attachment reaction can be carried out under relatively simple production conditions, and may even be accomplished by the end user, thus combining both manufacturing precision at the initial production stage, and assay flexibility at the ligand-addition stage.

Figure 7:
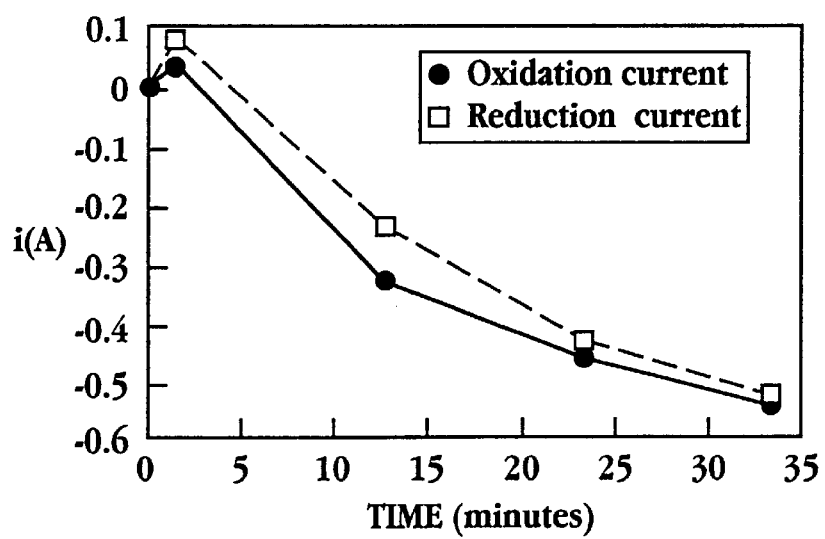
FIG. 7 shows the change in oxidation (solid circles) and reduction (open squares) current as a function of time after addition of E-coil peptide subunit to an electrode of the type illustrated in FIG. 5A containing an embedded K-coil peptide subunit.
Figure 8:
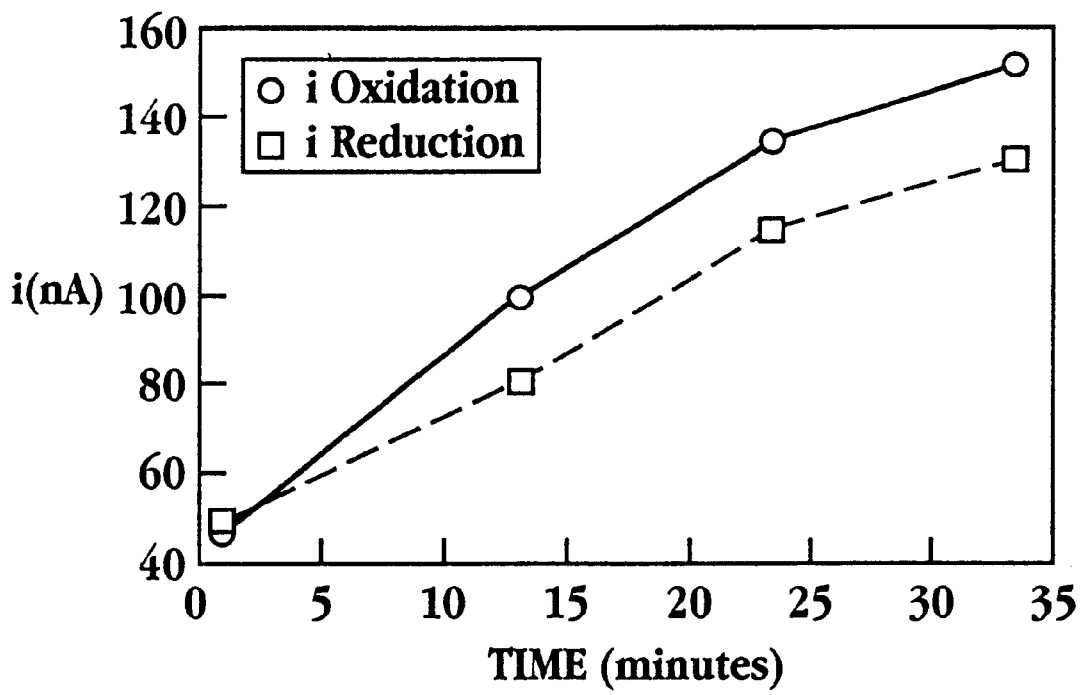
FIG. 8 shows changes in oxidation of $Fe(CN)_6^{3-/4-}$ (open circles) and reduction (open squares) as a function of time after addition of PAK peptide to an electrode containing di-saccharide ligands on a K-coil/E-coil lipid monolayer.
Figure 9:
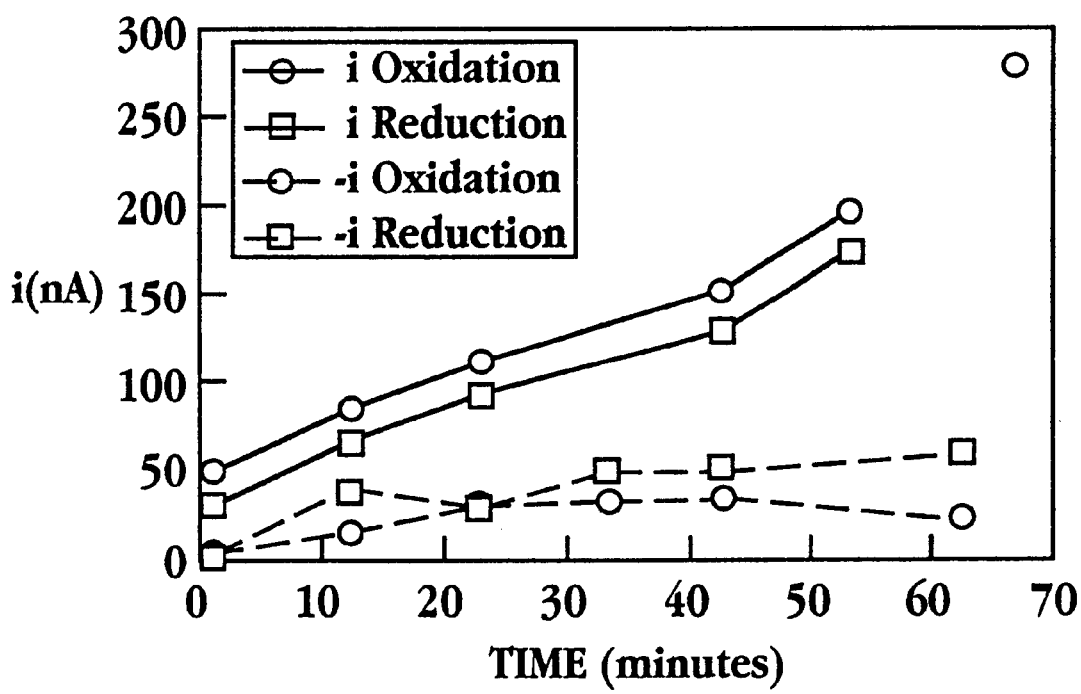
FIG. 9 shows changes in oxidation of $Fe(CN)_6^{3-/4-}$ (open circles) and reduction (open squares) as a function of time after addition of Verotoxin peptide to an electrode containing trisaccharide ligands on a K-coil/E coil lipid monolayer.

The invention is particularly useful in producing biosensor devices which use or require close-packed monolayer biosensor surfaces, as in the case of an amperometric biosensor. The studies reported in FIGS. 7–9 show that formation of heterodimers in a hydrocarbon-chain monolayer are compatible with a close-packed monolayer structure that forms an effective barrier to ion-carrier movement, and at the same time, is responsive to binding by a ligand-binding agent, to increase ion-carrier movement through the monolayer.

The invention is easily adapted to any of a variety of biosensor devices, such as those illustrated above. Further, the invention can be readily adapted to producing multi-ligand biosensors, by selectively contacting different regions of a universal biosensor surface with different selected HSP2-ligand conjugates.

In another aspect, the invention can be used to create multi-ligand assay surfaces by photomasking techniques that are capable of producing highly reproducible microarray biosensor devices having a plurality of different-ligand regions.

Although the invention has been described with respect to particular devices and methods, it will be understood that various changes and modifications can be made without departing from the invention, as encompassed by the accompanying claims.

It is claimed:

1. A biosensor apparatus for detecting a binding event between a ligand and ligand-binding agent, comprising
    means defining a biosensor surface,
    carried on said biosensor surface, two-subunit heterodimer complexes composed of first and second peptides that together form an α-helical coiled-coil heterodimer, where said first peptide is attached to the biosensor surface,
    a ligand covalently attached to the second peptide in the two-subunit heterodimer complexes, accessible for binding by a ligand-binding agent,
    means for introducing onto the biosensor surface, an analyte selected from the group consisting of a ligand-binding agent, and a ligand or ligand analog capable of competing with a ligand-binding agent for binding to said ligand, said apparatus also including a ligand-binding agent when the analyte is a ligand or ligand analog, and
    means for detecting the binding of a ligand-binding agent to the ligand on the biosensor surface.

2. An array device for detecting each of a plurality of binding events between a ligand and ligand-binding agent, comprising
    a substrate defining an array of surface regions,
    carried on each of said regions, two-subunit heterodimer complexes composed of first and second peptides that together form an α-helical coiled-coil heterodimer, where said first peptide is attached to the biosensor surface, and
    a ligand covalently attached to the second peptide in the two-subunit heterodimer complexes, accessible for binding by a ligand-binding agent.

3. The array device of claim 2, which is a biosensor device that includes a detector for detecting the binding of a ligand-binding agent to each of the array regions.

4. The array device of claim 3, wherein each surface region includes an electrode, and each of the electrodes is covered by a monolayer composed of 8–22 carbon atom chains attached at their proximal ends to the biosensor surface by a thiol linkage, and said chains have a molecular density of about 3 and 5 chains/nm$^2$.

5. The array device of claim 4, designed for amperometric detection of binding of a ligand-binding agent to the monolayer ligand, wherein the monolayer, including the heterodimer complexes, is sufficiently close-packed and ordered to form an effective barrier to current across the monolayer mediated by a redox ion species in an aqueous solution in contact with the monolayer, and binding of a ligand-binding agent to the ligand on the monolayer surface is effective to measurably increase the current across of the monolayer mediated by such redox species, the device further includes, for each array region, a chamber adapted to contain such an aqueous solution of redox species in contact with said monolayer, and the detector includes a circuit for measuring ion-mediated current across said monolayer, in response to binding events occurring between said receptor and ligand.

6. The array device of claim 3 designed for gravimetric detection of binding of different ligand-binding agents to selected regions in the array, wherein each of the array surface regions is a piezoelectric crystal, and the detector includes, for each surface region, means for generating a surface acoustic wave in said crystal and means for detecting the shift in wave frequency, velocity, or resonance frequency of the surface acoustic wave produced by binding of ligand-binding agent to said ligand.

7. The array device of claim 3, designed for optical surface plasmon resonance (SPR) detection of binding of different ligand-binding agents to selected regions in the array, wherein each of the array surface regions is a transparent dielectric substrate coated with a thin metal layer on which said monolayer is formed, said substrate and metal layer forming a plasmon resonance interface, and said detector includes means for exciting surface plasmons at a plasmon resonance angle that is dependent on the optical properties of the metal film and attached monolayer, and a detector for detecting the shift in plasmon resonance angle produced by binding of ligand-binding agent to said ligand.

8. The array device of claim 3, designed for optical detection of binding of a ligand-binding agent to the monolayer ligand, wherein said detector includes means for irradiating said monolayer with a light beam, and means for detecting a change in the optical characteristics of the monolayer produced by binding of ligand-binding agent to said ligand.

\* \* \* \* \*